United States Patent
Poor et al.

(10) Patent No.: US 10,143,574 B2
(45) Date of Patent: Dec. 4, 2018

(54) MONOLITHIC MEDICAL DEVICES, METHODS OF MAKING AND USING THE SAME

(71) Applicant: PALMAZ SCIENTIFIC, INC., Dallas, TX (US)

(72) Inventors: Michael Poor, Fremont, CA (US); Armando Garza, San Jose, CA (US); Scott Carpenter, Fremont, CA (US); Julio C. Palmaz, Napa, CA (US)

(73) Assignee: Vactronix Scientific, LLC, Fremont, CA (US)

( * ) Notice: Subject to any disclaimer, the term of this patent is extended or adjusted under 35 U.S.C. 154(b) by 0 days.

(21) Appl. No.: 14/213,974

(22) Filed: Mar. 14, 2014

(65) Prior Publication Data

US 2014/0296965 A1    Oct. 2, 2014

Related U.S. Application Data

(60) Provisional application No. 61/783,330, filed on Mar. 14, 2013, provisional application No. 61/788,767, filed on Mar. 15, 2013.

(51) Int. Cl.
*A61F 2/82* (2013.01)
*A61F 2/86* (2013.01)
(Continued)

(52) U.S. Cl.
CPC ............ *A61F 2/91* (2013.01); *A61F 2/915* (2013.01); *A61F 2002/068* (2013.01); *A61F 2002/823* (2013.01); *A61F 2002/91575* (2013.01)

(58) Field of Classification Search
CPC .......... A61F 2002/068; A61F 2002/823; A61F 2002/91575; A61F 2/91; A61F 2/915;
(Continued)

(56) References Cited

U.S. PATENT DOCUMENTS

| 4,733,665 A | 3/1988 | Palmaz | 128/343 |
| 5,102,417 A | 4/1992 | Palmaz | 606/195 |

(Continued)

FOREIGN PATENT DOCUMENTS

| WO | WO 2004/010902 | 2/2004 | A61F 2/06 |
| WO | WO 2010/124286 | 10/2010 | A61F 2/06 |
| WO | WO 2015/070124 | 5/2015 | A61F 2/89 |

OTHER PUBLICATIONS

PCT International Search Report issued in corresponding foreign application, pp. 1-3 (dated Aug. 6, 2014).
(Continued)

*Primary Examiner* — Seema Mathew
(74) *Attorney, Agent, or Firm* — David G. Rosenbaum; Benjamin D. Rotman; Rosenbaum IP, P.C.

(57) ABSTRACT

The monolithic device comprises a plurality of scaffolding members and a mesh patterned members webbed between the scaffolding members; the mesh patterned member webbed between the scaffolding members surround a lumen and generally expands from a contracted state to an expanded state; and mesh patterned members including a plurality of openings traversing the thickness of the mesh patterned member, and the mesh patterned members including a surface on which a pattern of openings is formed.

11 Claims, 12 Drawing Sheets

(51) Int. Cl.
*A61F 2/91* (2013.01)
*A61F 2/915* (2013.01)
*A61F 2/06* (2013.01)

(58) Field of Classification Search
CPC .. A61F 2002/91508; A61F 2002/91516; A61F 2002/91525; A61F 2002/91533; A61F 2002/91558; A61F 2002/91566; A61F 2002/91583; A61F 2230/0054; A61F 2250/0036; A61F 2/82; A61F 2/86; A61F 2/89; A61F 2/90
See application file for complete search history.

(56) References Cited

U.S. PATENT DOCUMENTS

| | | | | |
|---|---|---|---|---|
| 5,195,984 | A | 3/1993 | Schatz | 606/195 |
| 5,800,520 | A * | 9/1998 | Fogarty | A61F 2/07 |
| | | | | 606/194 |
| 7,594,927 | B2 | 9/2009 | Majercak et al. | 623/1.15 |
| 2002/0095207 | A1 | 7/2002 | Moriuchi et al. | 623/1.15 |
| 2002/0193862 | A1* | 12/2002 | Mitelberg | A61F 2/91 |
| | | | | 623/1.2 |
| 2003/0218735 | A1 | 11/2003 | Trozera | 355/104 |
| 2003/0225449 | A1* | 12/2003 | Denison | A61F 2/91 |
| | | | | 623/1.15 |
| 2004/0024445 | A1* | 2/2004 | Dickson | A61F 2/91 |
| | | | | 623/1.19 |
| 2004/0106985 | A1* | 6/2004 | Jang | A61F 2/91 |
| | | | | 623/1.16 |
| 2004/0230291 | A1* | 11/2004 | Richter | A61F 2/91 |
| | | | | 623/1.15 |
| 2004/0236404 | A1* | 11/2004 | Penn | A61F 2/91 |
| | | | | 623/1.15 |
| 2006/0086440 | A1* | 4/2006 | Boylan | A61F 2/915 |
| | | | | 148/563 |
| 2006/0224229 | A1* | 10/2006 | Goto | A61F 2/91 |
| | | | | 623/1.15 |
| 2008/0132989 | A1* | 6/2008 | Snow | A61F 2/95 |
| | | | | 623/1.12 |
| 2008/0294239 | A1* | 11/2008 | Casey | A61F 2/91 |
| | | | | 623/1.16 |
| 2010/0087913 | A1* | 4/2010 | Rabkin | A61F 2/91 |
| | | | | 623/1.16 |
| 2010/0249904 | A1* | 9/2010 | Takayuki | A61F 2/91 |
| | | | | 623/1.16 |
| 2011/0022157 | A1* | 1/2011 | Essinger | A61F 2/2418 |
| | | | | 623/1.26 |
| 2012/0009325 | A1 | 1/2012 | Storment | 427/2.25 |
| 2012/0136427 | A1 | 5/2012 | Palmaz et al. | 623/1.15 |
| 2012/0209366 | A1* | 8/2012 | Sudo | A61F 2/91 |
| | | | | 623/1.11 |
| 2012/0282391 | A1 | 11/2012 | Palmaz et al. | 427/2.25 |
| 2012/0310319 | A1 | 12/2012 | Tieu et al. | 623/1.4 |
| 2013/0268055 | A1* | 10/2013 | Cottone | A61F 2/915 |
| | | | | 623/1.16 |
| 2014/0042022 | A1 | 2/2014 | Xu et al. | 204/298.15 |
| 2014/0109383 | A1 | 4/2014 | Carpenter et al. | 29/527.2 |
| 2014/0114435 | A1 | 4/2014 | Carpenter et al. | 623/23.76 |
| 2015/0112422 | A1* | 4/2015 | Pazienza | A61F 2/915 |
| | | | | 623/1.16 |
| 2017/0035589 | A1* | 2/2017 | Carpenter | A61F 2/013 |
| 2017/0079816 | A1* | 3/2017 | Komatsu | A61F 2/04 |

OTHER PUBLICATIONS

PCT Preliminary Report on Patentability issued in corresponding foreign application, pp. 1-12 (dated Sep. 24, 2015).
European Search Report issued in corresponding foreign application, pp. 1-8 (dated Nov. 11, 2016).

* cited by examiner

MONOLITHIC MEDICAL DEVICES, METHODS OF MAKING AND USING THE SAME

CROSS-REFERENCE TO RELATED APPLICATIONS

The application claims priority to U.S. Provisional Application Ser. No. 61/783,330, filed Mar. 14, 2013 and U.S. Provisional Application Ser. No. 61/788,767, filed Mar. 15, 2013, all herein incorporated by reference in their entireties.

BACKGROUND

The invention generally relates to medical devices.

Various types of intravascular stents have been used in recent years. An intravascular stent generally refers to a device used for the support of living tissue during the healing phase, including the support of internal structures. Intravascular stents, or stents, placed intraluminally, as by use of a catheter device, have been demonstrated to be highly efficacious in initially restoring patency to sites of vascular occlusion. Intravascular stents, or stents, may be of the balloon-expandable type, such as those of U.S. Pat. Nos. 4,733,665; 5,102,417; or 5,195,984, which are distributed by Johnson & Johnson Interventional Systems, of Warren, N.J., as the Palmaz™ and the Palmaz-Schatz™ balloon-expandable stents or balloon expandable stents of other manufacturers, as are known in the art. Other types of intravascular stents are known as self-expanding stents, such as Nitinol coil stents or self-expanding stents made of stainless steel wire formed into a zigzag tubular configuration.

Prior art stents have some functional limitations due to their current design. For example, the prior art stent can collapse when it is bent around a sharp angle. What is needed is an improved stent that is more flexible and can be implanted in tightly bent vessels.

SUMMARY OF THE INVENTION

Provided herein are systems, methods and compositions for monolithic medical devices and methods making and using the same.

The methods, systems, and apparatuses are set forth in part in the description which follows, and in part will be obvious from the description, or can be learned by practice of the methods, apparatuses, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the methods, apparatuses, and systems, as claimed.

BRIEF DESCRIPTION OF THE DRAWINGS

In the accompanying figures, like elements are identified by like reference numerals among the several preferred embodiments of the present invention.

DETAILED DESCRIPTION OF THE INVENTION

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

In one aspect, the present invention comprises a monolithic medical device and a method of making monolithic medical devices.

Figure 3A:
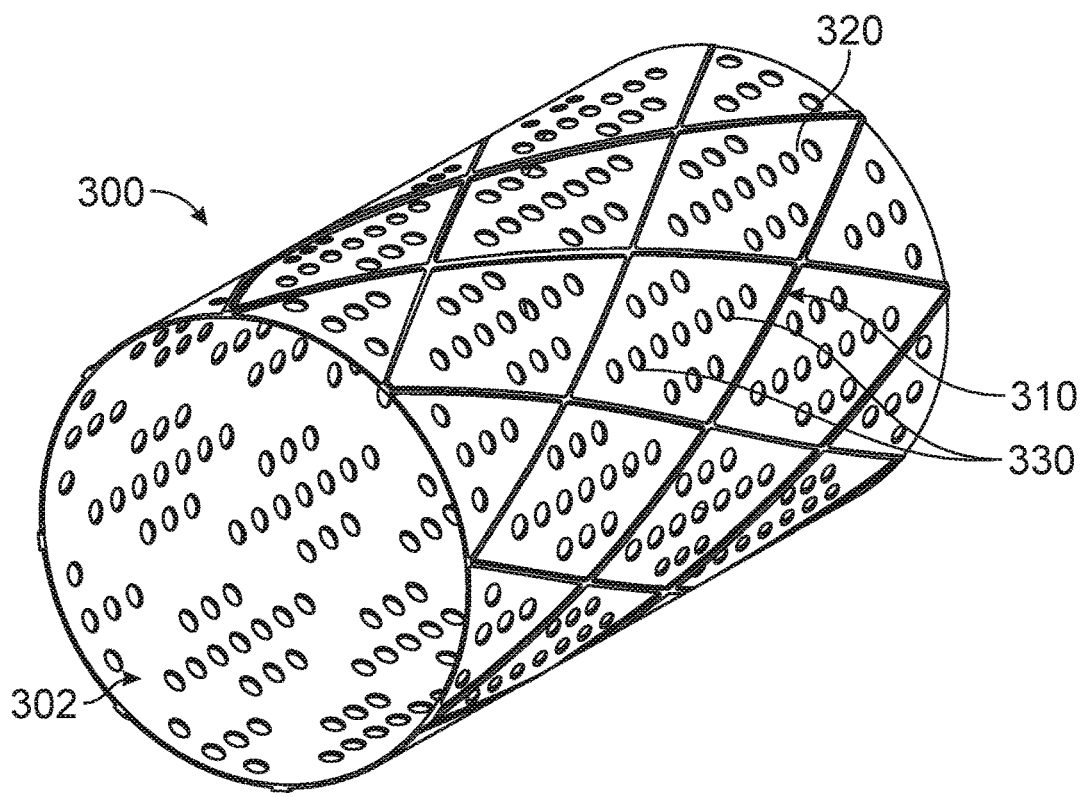
FIG. 3A is a perspective view of one embodiment of a monolithic medical device.

Generally speaking, the monolithic device may comprise a covered stent 300, as shown in FIG. 3A. In one embodiment, the monolithic device can be used to prevent plaque from embolizing downstream during a stent placement. The covered (or webbed) stent 300 comprises of a plurality of scaffolding members 310 and a mesh patterned members 320 webbed between the scaffolding members 310. The mesh patterned member 320 webbed between the scaffolding members 310 surround a lumen 302 and may generally expand from a contracted state to an expanded state. The scaffold members 310 may generally for polygonal shapes, including, but not limited to, squares, rectangles, trapezoids, pentagons, diamond-shapes, hexagons, octagons, circles, ellipses, and the like. The mesh patterned member 320 may general includes a plurality of openings 330 traversing the thickness of the mesh patterned member 320. The mesh patterned members 320 includes a surface on which a pattern of openings 330 is formed. The covered stent 300 can be monolithically constructed out of one starting work-piece tube using subtractive processing. The covered stent made monolithically is favored due the fact that the tedious and often questionable joining/assembly of the two components as historically achieved could possibly be circumvented, in-turn potentially improving quality and performance while reducing overall costs. The monolithically constructed covered stent ensures a secure bond between the scaffolding members 310 and the mesh patterned member 320 webbed between the scaffolding members 310 about the entire length and circumference of the device.

Figure 1:
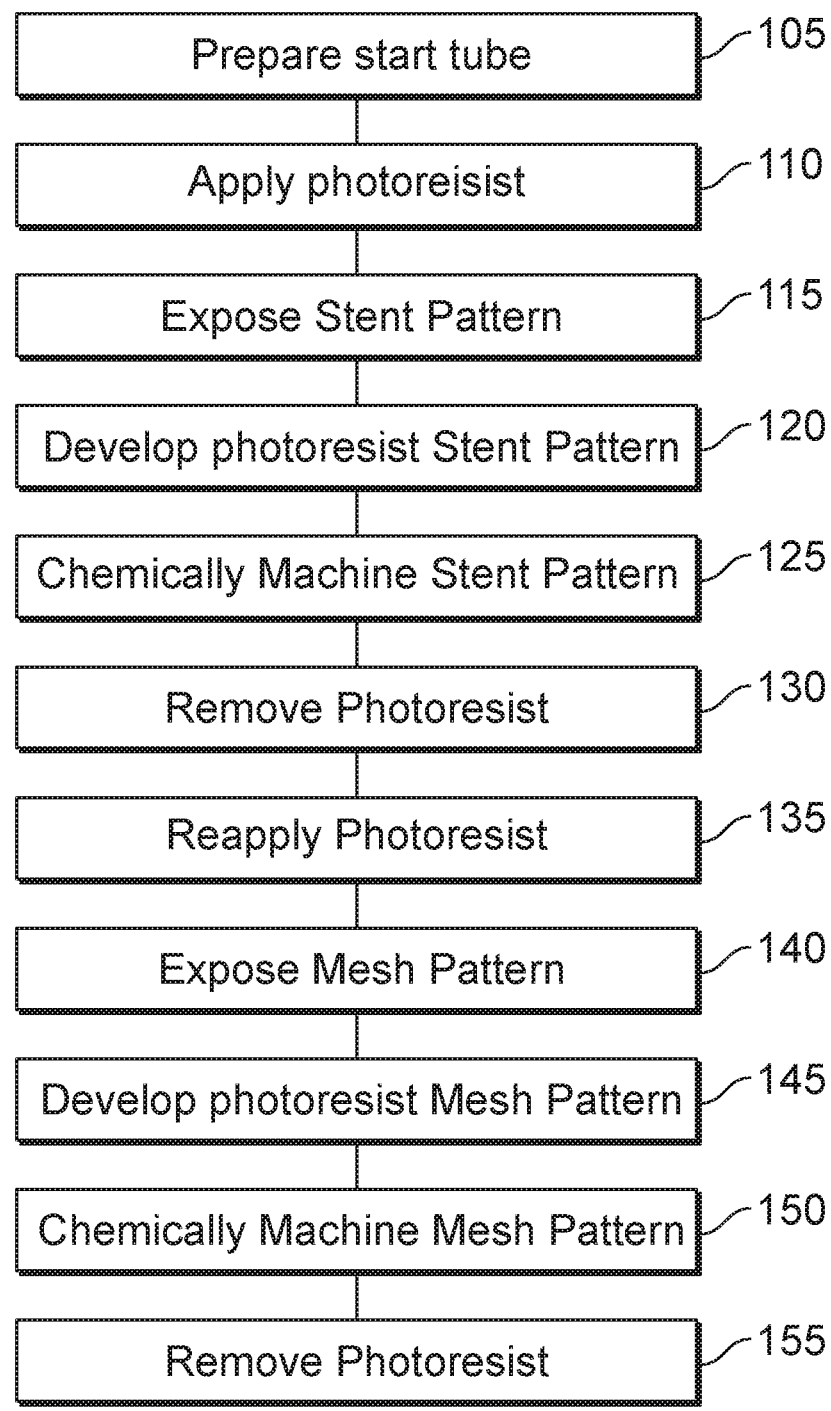
FIG. 1 is a diagram of one embodiment of a method to make a monolithic medical device.

FIG. 1 highlights the process flow steps 100 of how the monolithic covered stent may be made according to one embodiment. A start tube is prepared 105, and then photoresist is applied to the start tube 110. The start tube may be a wrought metal, polymer, composite, or ceramic tube, or may be vacuum deposited metal or polymer tube. The start tube may be fabricated by a deposition procedure as disclosed in commonly assigned U.S. patent application Ser. No. 13/788,081, filed Mar. 7, 2013 or in U.S. patent application Ser. No. 13/099,980, filed May 3, 2011, herein incorporated by reference in their entireties. Alternatively, the monolithic device may be produced from drawn metal or polymer tubing, or wrought tubing, provided that fatigue life is adequate. Radiopaque markers could be added as an interdispersed deposited layer or a ternary alloy deposition (e.g., NiTiTa or NiTiNb) if vacuum deposition is used. Different metal layers may be used to form the monolithic device. The positioning of the layers can be optimized for mechanical, or other reasons. Furthermore, ternary additions to binary Nitinol can be used to strengthen or otherwise alter the material properties, allowing for lower profile devices, enhanced fatigue resistance, etc. These ternary additions can also double as radiopacity enhancers. The stent pattern is then exposed 115 and the stent pattern's exposed photoresist is developed 120. Methods for UV exposure of the pattern (stent or mesh) can include using contact mask methods, non-contact methods (e.g., DLP pattern projection), or UV laser writing. Then the stent pattern is chemically machined 125, and the photoresist is removed 130. Photoresist is then reapplied 135, and the mesh pattern is exposed 140. The exposed photoresist for the mesh pattern members is developed 142, and the mesh pattern members are chemically machined 144. The final step is to remove the photoresist 146. Photo-chemical machining enables the tiered levels of tube wall material from which the stent scaffold and fine mesh patterned members can be made. Steps 105 through 130 shown in FIG. 1 detail how the larger scaffolding patterns of a stent may be chemically machined to achieve a partial through-wall pattern. It is preferred that the photoresist be coated electro-phoretically due to the nature of the coating process that results in uniform and even conformal coatings over complex 3D work-piece geometries. Steps 135 through 146 highlight methods for machining the fine mesh pattern(s) within the cells of the larger stent struts either by using photo-chemical or laser machining The machining and patterning herewith may use the methods of commonly assigned U.S. patent application Ser. No. 13/801, 173, filed Mar. 13, 2013, incorporated by reference herein in its entirety. Alternatively, the mesh pattern members may include grooved features along with the openings on at least one surface of the monolithic device. In other embodiments, the pattern may be a plurality of microgrooves imparted onto the luminal and/or abluminal surface of the monolithic device, as is more fully described in U.S. patent application Ser. No. 13/654,923, filed Oct. 18, 2012, which is commonly assigned with the present application and is hereby incorporated by reference in its entirety. The plurality of microgrooves may be formed either as a post-deposition process step, such as by etching, or during deposition, such as by depositing the stent-forming material onto a mandrel which has a microtopography on the surface thereof which causes the metal to deposit with the microgroove pattern as part of the deposited material.

Figure 2:
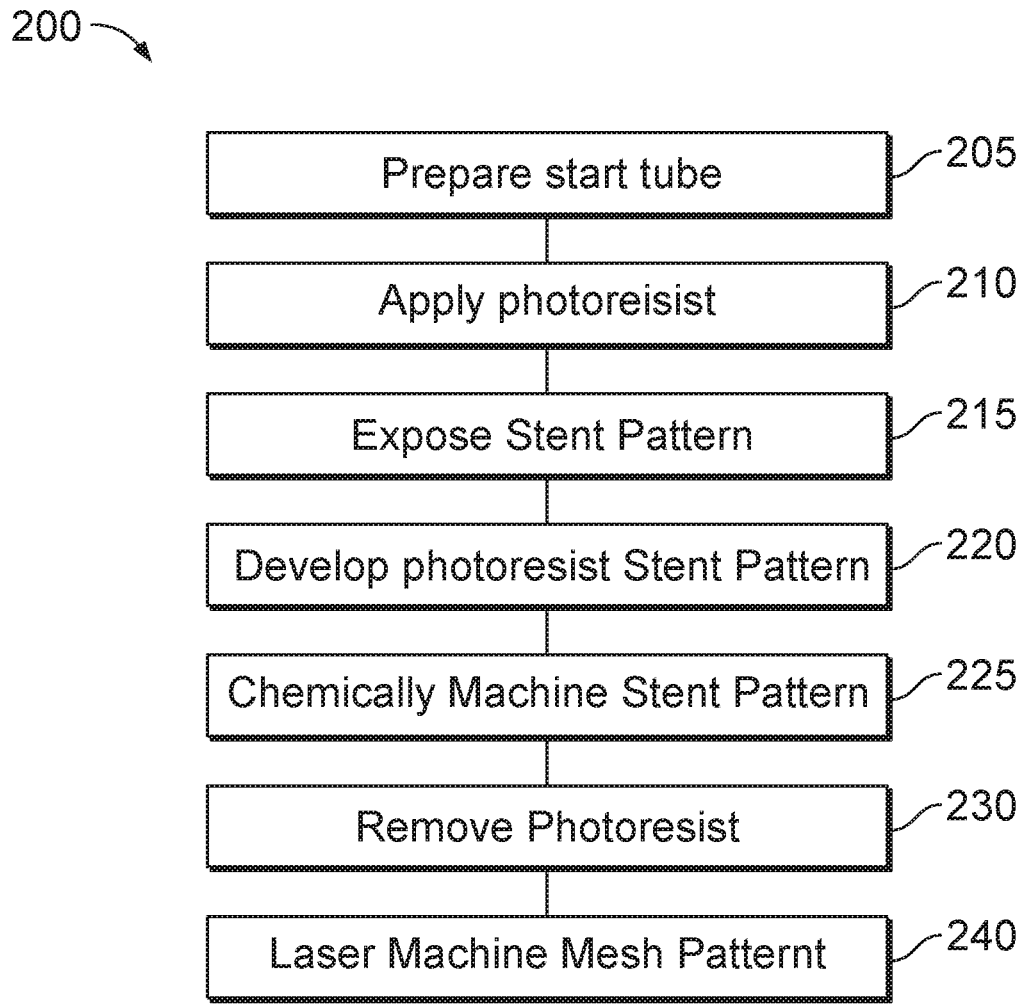
FIG. 2 is a diagram of one embodiment of a method to make a monolithic medical device.

An alternative process 200 is shown in FIG. 2, which comprises the preparation of the start tube 205, and applying a photoresist to the start tube 210. Then, the stent pattern is exposed 215 and the photoresist is developed for the stent pattern 220. The stent pattern is then chemically machined 225, and the photoresist is removed 230. The last step is to laser machine the mesh pattern 240.

The processes 100 and 200 previously mentioned include the use of electrophoretically depositable (ED) photoresist, and photochemical machining of a 3D work-piece geometry to make the monolithic medical device. The use of ED photoresist allows for pattern designs that encompass different circumferential planes, which is necessary for the monolithic covered stent to resolve the stent and mesh patterns. Through the methods 100 and 200 disclosed above, a vast assortment of stent and mesh patterns may be formed which enable optimal designs.

Although it is preferable that the photoresist be applied to the work-piece tube (or other geometry) electrophoretically using either an anionic or cationic electrophoretic depositable photoresist, the photoresist may be applied using other techniques including but not limited to lamination, spraying, dipping, or Chemical Vapor Deposition (CVD). Although chemical machining has been initially disclosed as the method for through-resist machining, other selective methods including but not limited to reactive ion etching (RIE), dry etching, electrochemical machining, or photo-activated chemical machining may be used. RIE may utilize Cl or F (or mixtures thereof) based chemistries or others compatible with etching SS, PtCr, Nitinol, SS, CoCr alloys (to include MP35N and L-605). Dry etching may use inert gases such as Ar, Kr, Xe, and the like.

Figure 3B:
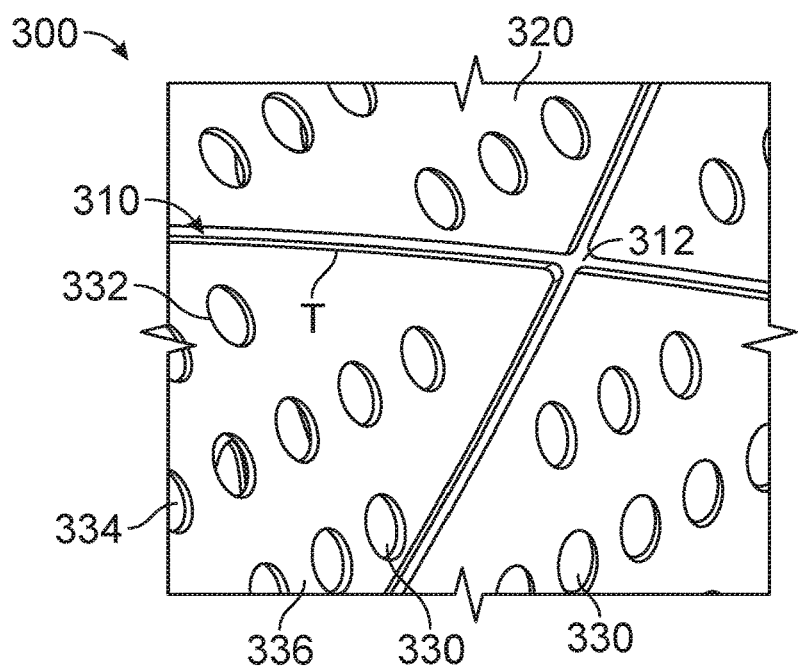
FIG. 3B is an enlarged view of a section of the device of FIG. 3A, showing the scaffolding members and the mesh patterned members.

As shown in FIG. 3B, the device 300 includes a plurality of scaffold members 310 and mesh patterned members 320 webbed between the scaffolding members 310. The scaffolding members 310 may include a raised surface feature that includes a thickness T above the surface of the mesh patterned members 320. The mesh patterned members 320 may form generally polygonal shapes with the scaffolding members 310 forming the borders thereabout. A plurality of openings 330 may be patterned in a first row 332, a second row 334, and/or a third row 336 in the mesh patterned members 320. The scaffolding members 310 may intersect at points 312 to form larger hinge regions 312 to allow for the expansion of the scaffolding members 310. In one embodiment, the mesh patterned members 320 have a length or a width between at least 0.1 to 50.0 microns in length or width, alternatively between at least 10.0 to 100.0 microns in length or width, or alternatively between at least 1.0 to 1000.0 microns in length or width. The length and/or width of the mesh patterned members 320 may be selected according to the type of pattern and openings employed with the mesh patterned members.

Figure 4A:
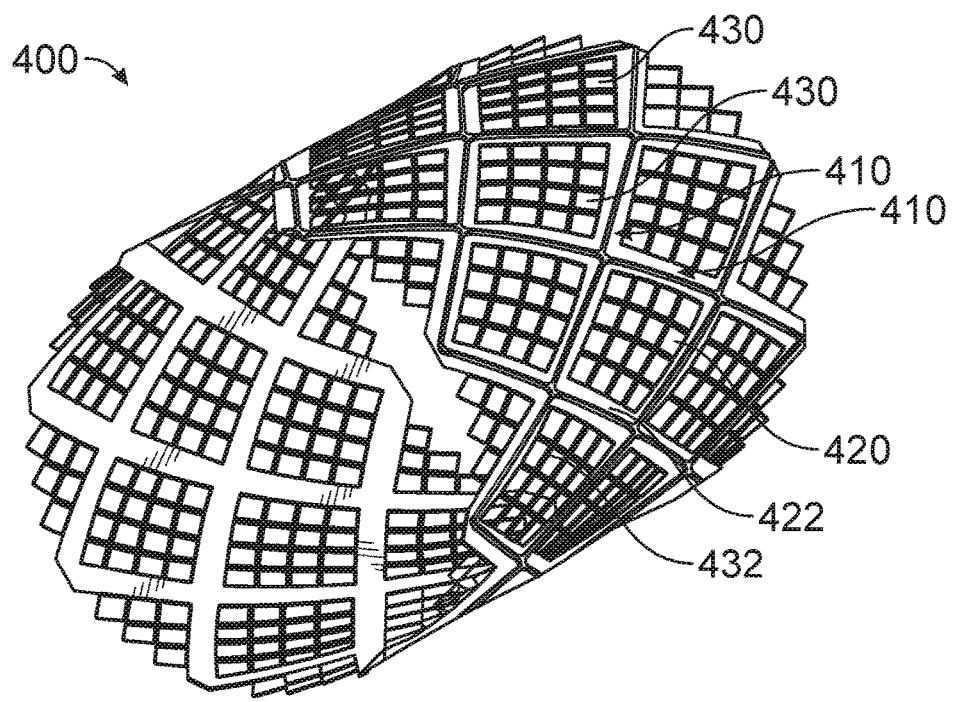
FIG. 4A is a perspective view of one embodiment of a monolithic medical device.
Figure 4B:
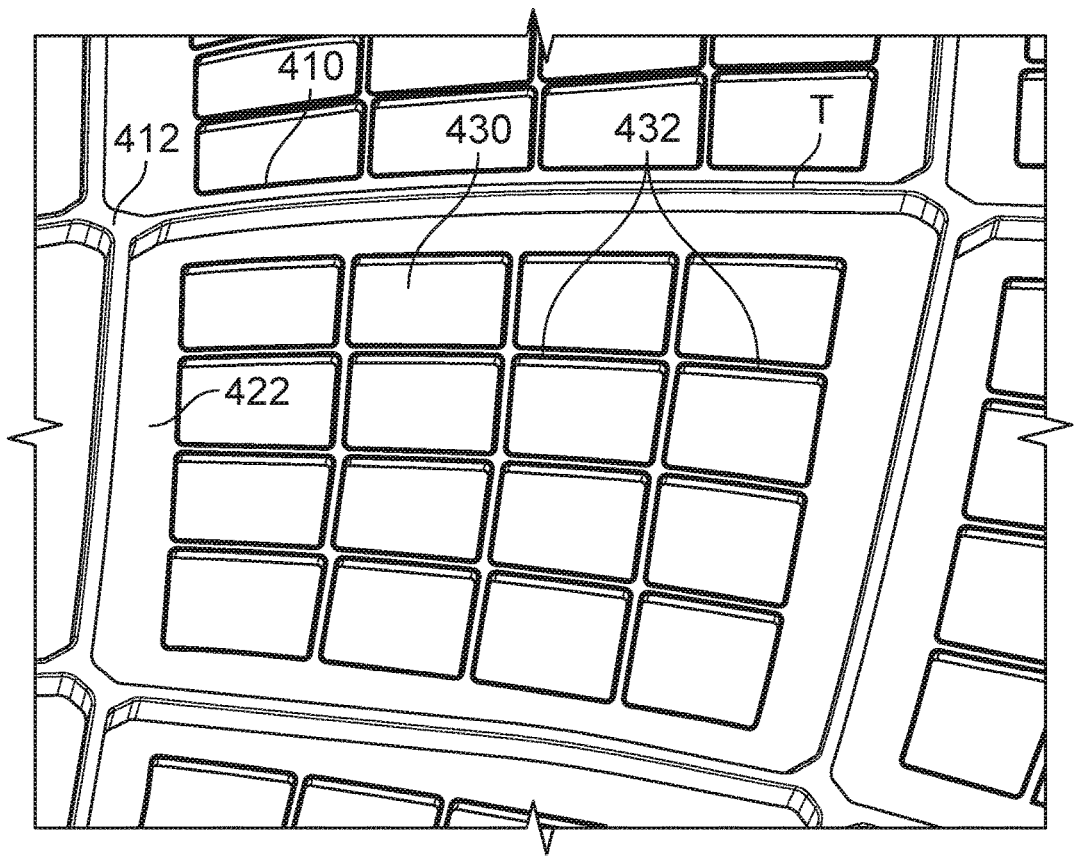
FIG. 4B is an enlarged view of a section of FIG. 4A showing the scaffold members and the mesh patterned members.

An alternative embodiment of the monolithic medical device 400 is shown in FIGS. 4A-4B. The monolithic medical device 400 comprises a plurality of scaffold members 410 interconnected by a plurality of mesh patterned members 420. The mesh patterned members 420 may include a plurality of openings 430 throughout the surface of the mesh patterned members 420, and exterior borders 422 around the perimeters of the mesh patterned members 420, as shown in FIG. 4B. The plurality of openings 430 may generally form a diamond shaped pattern 432. The generally diamond shaped pattern 432 may generally include between at least 4 to 16 openings 430 in a mesh patterned member 420. Generally, the scaffold members 410 include a thickness T that is raised from the surface of the mesh patterned members 420, and the scaffold members 410 intersect at hinge regions 412.

Figure 5A:
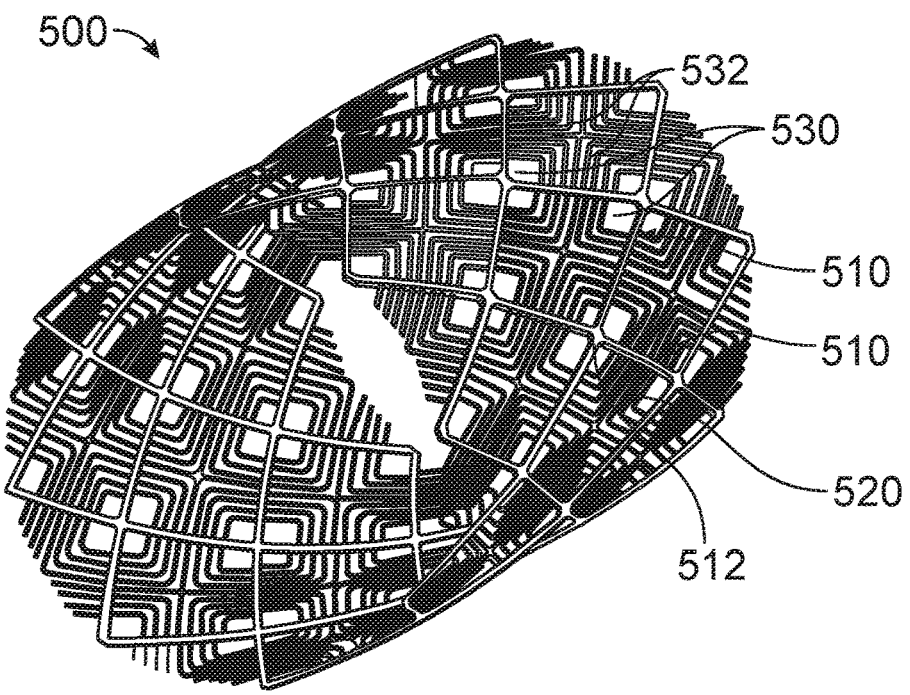
FIG. 5A is a perspective view of one embodiment of the monolithic medical device.
Figure 5B:
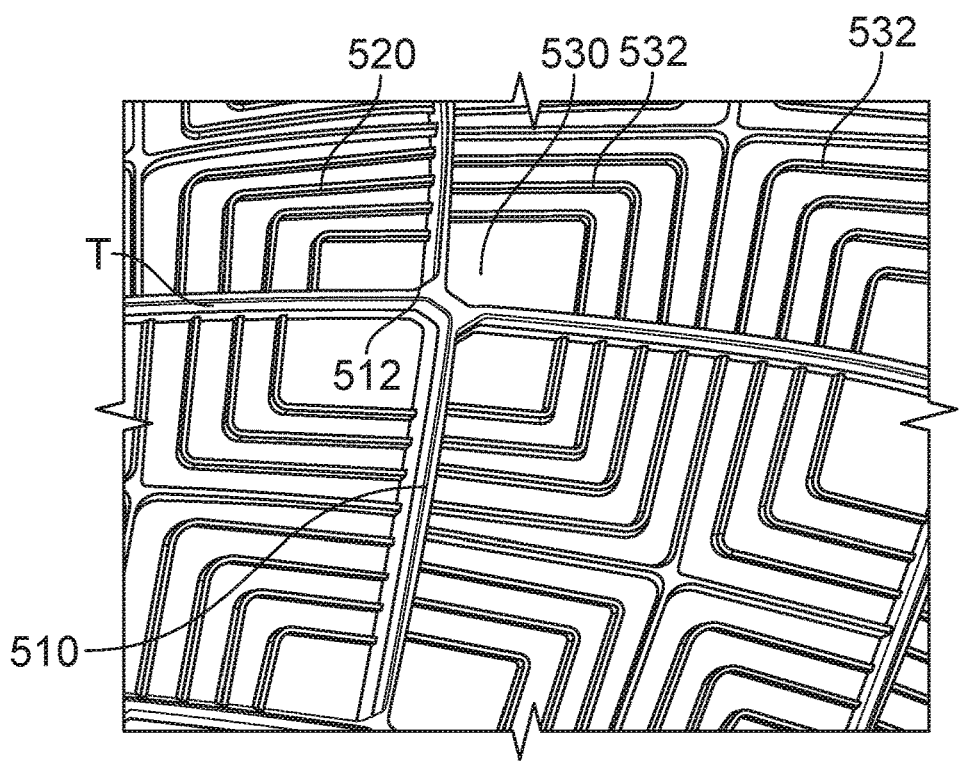
FIG. 5B is an enlarged view of a section of FIG. 5A showing the scaffold members and the mesh patterned members.

An alternative embodiment of the monolithic medical device 500 is shown in FIGS. 5A-5B. The monolithic medical device 500 may comprise a plurality of scaffold members 510 interconnected by a plurality of mesh patterned members 520. The mesh patterned members 520 may include a plurality of openings 530 in the corner features of the mesh patterned members 520, and a plurality of L-shaped openings 532 traversing the width and length of the mesh patterned members 520. In one embodiment, each corner opening 530 includes at least 2 to 5 L-shaped openings 532 of progressively larger L-shapes. As shown in FIG. 5B, corner openings 530 adjacent to scaffold members 510 may be a different size. Generally, the scaffold members 510 include a thickness T that is raised from the surface of the mesh patterned members 520, and the scaffold members 510 intersect at hinge regions 512.

Figure 6A:
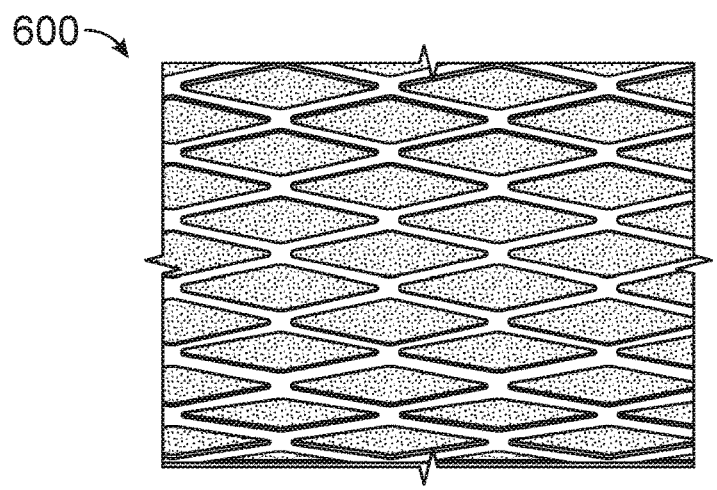
FIGS. 6A-6B, are enlarged photographs of the photoresist and the exposed metal from the metal tube 600 is shown after steps 105 through 120 and steps 205 through 220 from FIGS. 1-2, at 100× magnification.
Figure 6B:
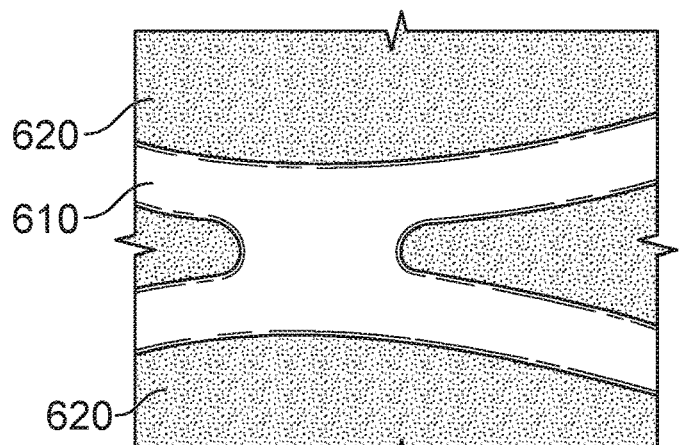
Figure 6C:
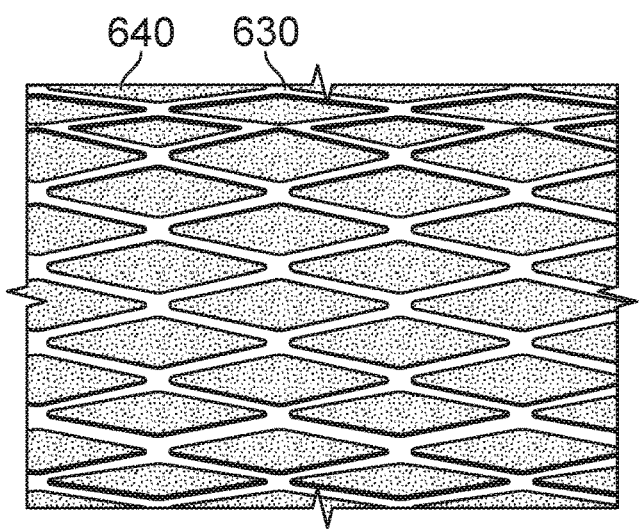
FIG. 6C shows an embodiment of the device after steps 125 through 130 and steps 225 through 230 from FIGS. 1-2, displaying the scaffolding members and mesh surface that can be later patterned by laser machining or chemically machining

As shown in FIGS. 6A-6B, the photoresist and the exposed metal from the metal tube 600 are shown after steps 105 through 120 and steps 205 through 220. The exposed photoresist 610 defines the location of the scaffold members and the exposed metal 620 is shown for locations of the mesh pattern members. FIG. 6C shows the result of steps 125 through 130 and steps 225 through 230, displaying the scaffold members 630 and mesh pattern surface 640 that can be later patterned by laser machining or chemical machining The monolithic device may be used with any type of cell, which cell has a cellular membrane. Most distinct cell types arise from a single totipotent cell that differentiates into hundreds of different cell types during the course of development. Multicellular organisms are composed of cells that fall into two fundamental types: germ cells and somatic cells. During development, somatic cells will become more specialized and form the three primary germ layers: ectoderm, mesoderm, and endoderm. After formation of the three germ layers, cells will continue to specialize until they reach a terminally differentiated state that is much more resistant to changes in cell type than its progenitors. The ectoderm differentiates to form the nervous system (spine, peripheral nerves and brain), tooth enamel and the epidermis (the outer part of integument). It also forms the lining of mouth, anus, nostrils, sweat glands, hair and nails. The endoderm forms the gastrointestinal tract cells, the respiratory tract cells, the endocrine glands and organ cells, the auditory system cells, and the urinary system cells. The mesoderm forms mesenchyme (connective tissue), mesothelium, non-epithelial blood cells and coelomocytes. Mesothelium lines coeloms; forms the muscles, septa (cross-wise partitions) and mesenteries (length-wise partitions); and forms part of the gonads (the rest being the gametes).

The inventive monolithic devices may be intravascular stents, stent-grafts, grafts, heart valves, venous valves, filters, occlusion devices, catheters, sheaths, osteal implants, implantable contraceptives, implantable antitumor pellets or rods, shunts and patches, pacemakers, needles, temporary fixation rods, medical wires or medical tubes for any type of medical device, or other implantable medical devices, as will also be hereinafter described. A pacemaker (or artificial pacemaker, so as not to be confused with the heart's natural pacemaker) is a medical device that uses electrical impulses, delivered by electrodes contacting the heart muscles, to regulate the beating of the heart. The electrodes may be covered by tubing or other material that includes a surface that may require endothelialization and grooves thereon. Earrings and other piercings may benefit from the topographical features, as well as any other implant, whether the implant is an organic, inorganic, mechanical, electrical, or biological device.

In some embodiments, the monolithic device is formed from a metal, a polymer, a composite, or a ceramic material. In some embodiments, materials to make the inventive stents are chosen for their biocompatibility, mechanical properties, i.e., tensile strength, yield strength, and their ease of deposition include the following: elemental titanium, vanadium, aluminum, nickel, tantalum, zirconium, chromium, silver, gold, silicon, magnesium, niobium, scandium, platinum, cobalt, palladium, manganese, molybdenum and alloys thereof, such as zirconium-titanium-tantalum alloys, nitinol, and stainless steel.

In another aspect, the present invention may comprise a monolithic medical device and a method of using the monolithic medical device.

Figure 7:
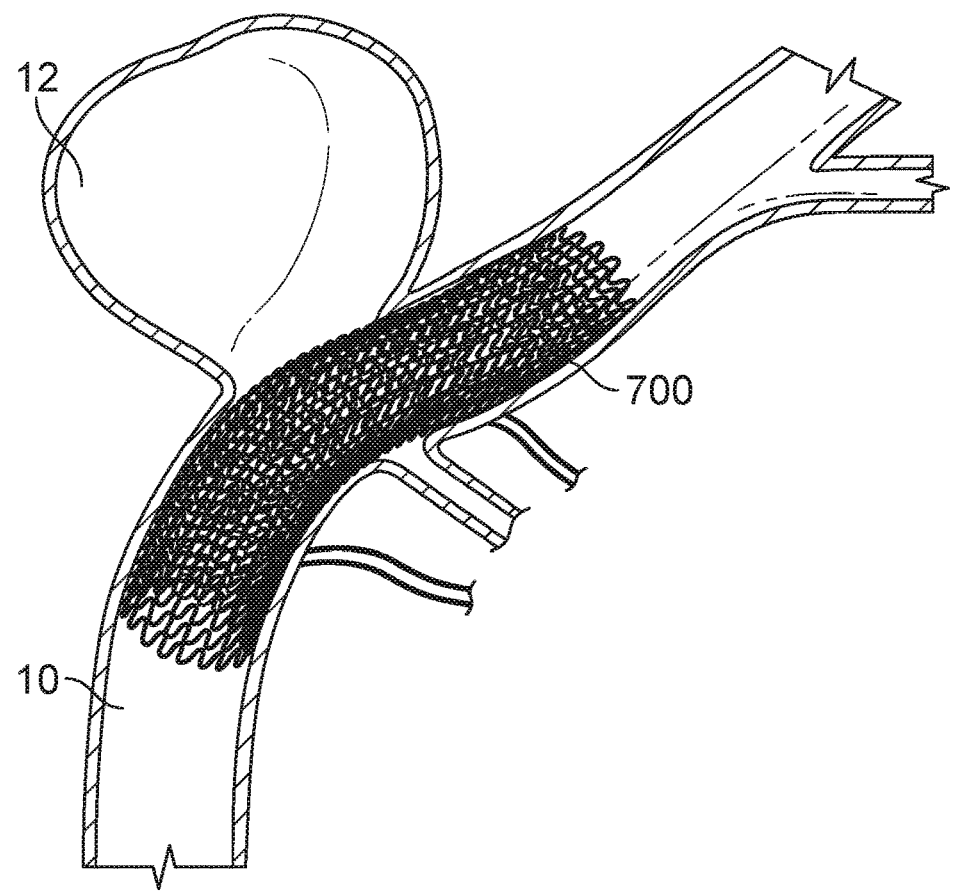
FIG. 7 is a perspective view of one embodiment of a monolithic device preserving flow in a blood vessel while diverting flow from an aneurysm.
Figure 8A:
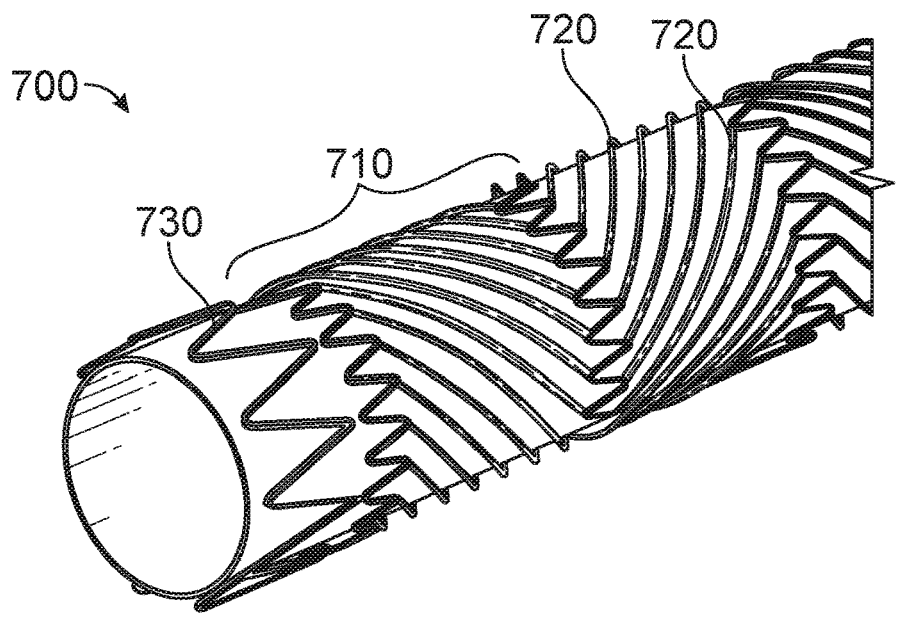
FIG. 8A is a perspective view of one embodiment the monolithic device.

Generally speaking, the monolithic device 700 may comprise a low profile stent that promotes thrombosis of an aneurysm 12 by diverting blood flow through the parent vessel 10, as shown in FIG. 7. As shown in FIG. 8A, the monolithic device 700 comprises an ultra-dense stent cell pattern 710 including a plurality of structural members 720 that diverts the majority of blood flow without restricting blood flow completely, thus providing the opportunity for the aneurysm to shrink over time. The monolithic device includes an expanded state and a contracted state for delivery. The monolithic device may include an end ring 730 on the proximal and/or distal ends. This monolithic device may alternatively be used as an embolic protection stent cover or in any other application where a low profile, high density pattern is desirable. Alternatively, the monolithic device may be used a liner for a catheter tip, scaffold/indenter for drug-eluting balloons, and vascular stenting, including; vulnerable plaque containment (carotid, coronary), flow diversion, adjunct to coiling (neurological), and vascular perforation.

Figure 8B:
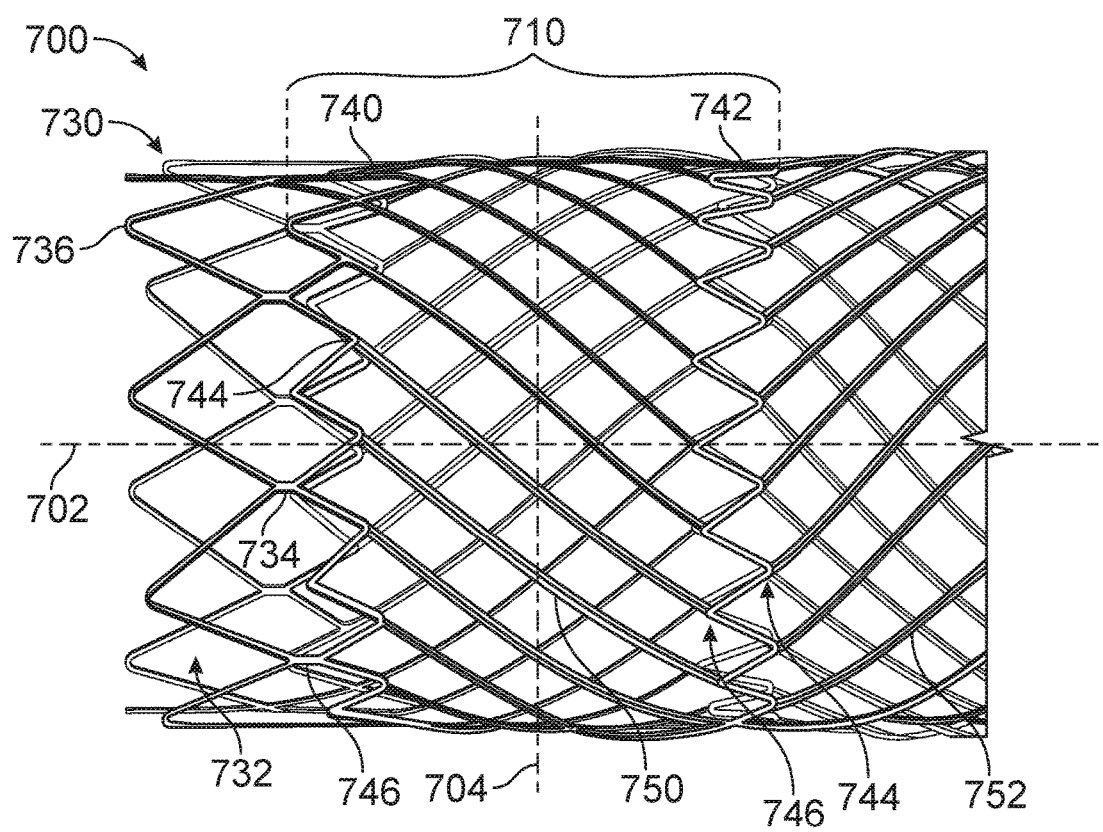
FIG. 8B is an enlarged view of a photograph of the distal end of one embodiment of the monolithic device, in the expanded configuration at 50× magnification.
Figure 8C:
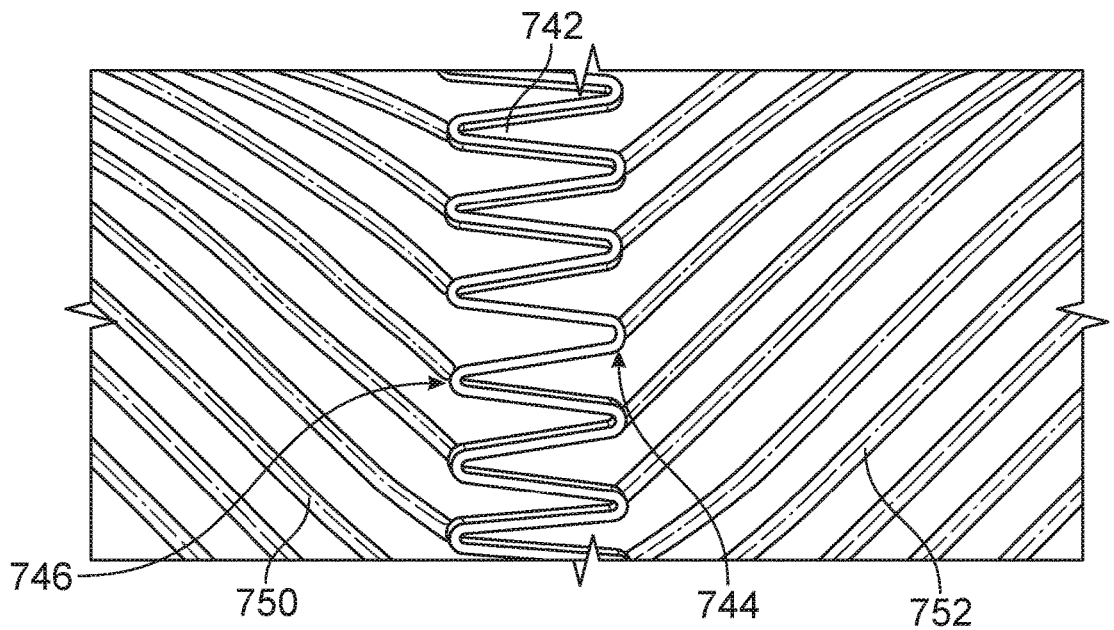
FIG. 8C is an enlarged view of a photograph of the embodiment of the monolithic device of FIG. 8B, in the unexpanded configuration at 100× magnification.

As shown in FIG. 8B, the expanded monolithic device 700 includes the end ring 730 on either the proximal or distal end or both ends of the device 700. The ultra-dense cell pattern 710 includes a first Z-pattern 740 of the structural members 720 and a second Z-pattern 742 of the structural members 720. The first and second Z patterns 740, 742 form a plurality of peaks 744 and a plurality of troughs 746 along the longitudinal axis 702. The first and second Z patterns 740, 742 are interconnected by a plurality of curved interconnecting members 750 that connect a peak 744 of the first Z pattern 740 with a trough 746 of the second Z pattern 742. Preferably, the curved interconnecting members 750 do not connect adjacent peaks 744 of the first Z pattern to adjacent troughs 746 of the second Z pattern. In one embodiment, the curved interconnecting members 750 connect a peak 744 of the first Z pattern with a trough 746 of the second Z pattern that is displaced along the longitudinal axis and at least one trough below the peak 744 along the vertical axis 704 of the monolithic device 700. In other embodiments, the curved interconnecting members 750 may connect a peak 744 of the first Z pattern 740 with a trough 746 of the second Z pattern 742 that is at least two troughs below the peak 744 along the vertical axis 704 of the monolithic device. This connection of the peak 744 of the first Z pattern 740 with a nonadjacent trough 746 of the second Z pattern 742 by the curved interconnecting member 750 forms the curved portion of the curved interconnecting member 750. As shown in FIGS. 8B-8C, the second Z pattern 742 is connected with a second set of curved interconnecting members 752 at the peak 744 that is angled at an opposite angle or non-parallel angle from the first set of the curved interconnecting members 750. The opposite or non-parallel angle may be between about 10-100 degrees, alternatively, between about 20-90 degrees, alternatively, between about 30-80 degrees. The tight first and second Z patterns 740, 742 allow the monolithic device to maintain adequate radial force despite its small size. The interior cell structure 710 could be modified to optimize performance.

Figure 8D:
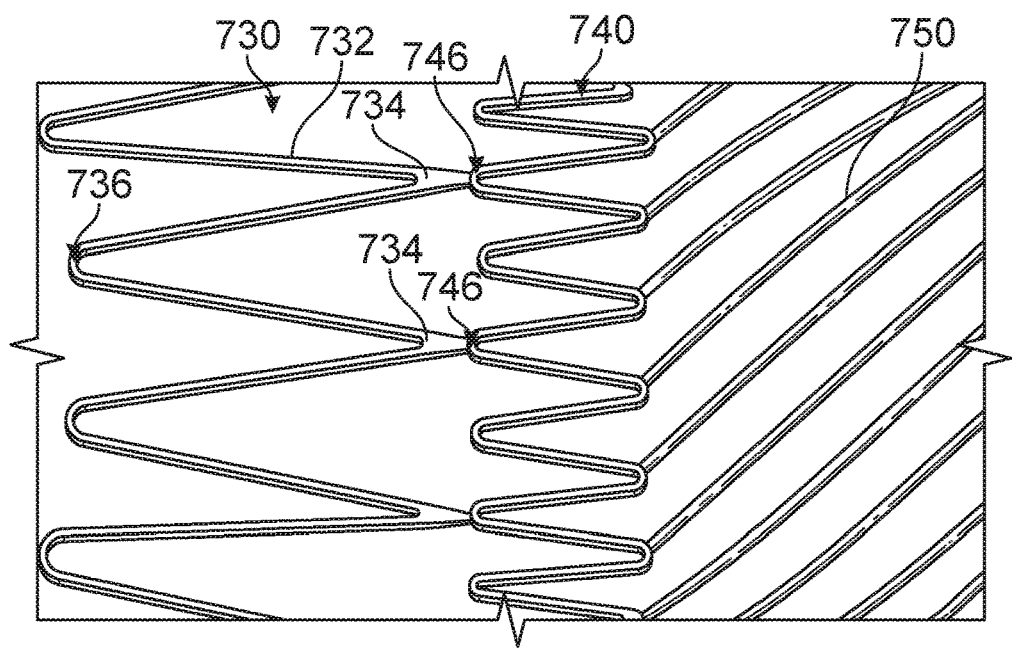
FIG. 8D is an enlarged view of a photograph of the distal end of the embodiment of the monolithic device of FIG. 8B, in the unexpanded configuration at 100× magnification.

As shown in FIGS. 8B-8D, the end ring 730 includes an end Z pattern 732 comprising a plurality of peaks 734 and a plurality of troughs 736. In one embodiment, a peak 734 of the end ring 730 connects to every other trough 746 of the first Z pattern 740, such that the peak 734 of each end Z pattern 730 does not connect to adjacent troughs 746 of the first Z pattern 740. This connection forms a larger end Z pattern 732. In one embodiment, the peak 734 of the end Z pattern 732 connects to every third trough 746 of the first Z pattern 740, while in other embodiments the peak 734 may connect to every fourth trough 746 of the first Z pattern 740. The modified end rings of the stent geometry can prevent cell migration as well as be used for marker placement. Alternatively, the end rings could be modified or eliminated completely from the monolithic device.

Figure 9:
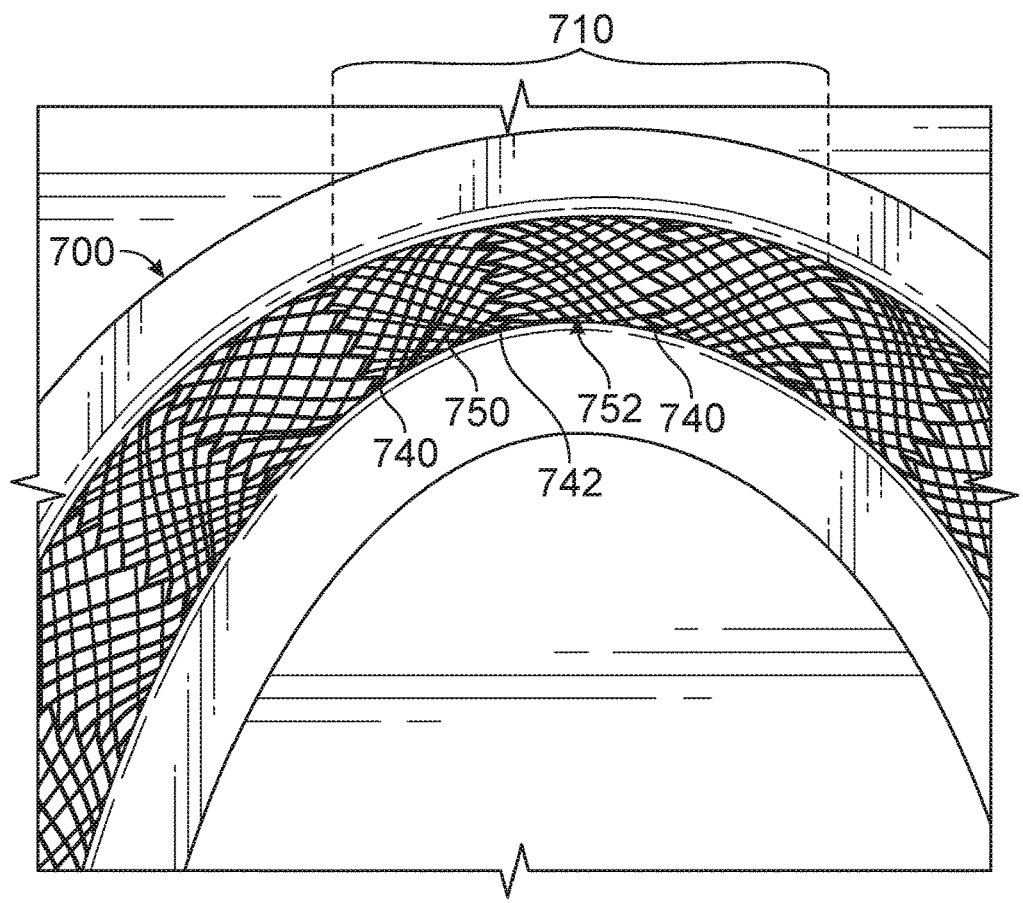
FIG. 9 is an enlarged view of a photograph of one embodiment of the monolithic device in a bent configuration.

As shown in FIG. 9, the monolithic device 700 may be bent along its longitudinal axis to conform to the shape or curvature of a blood vessel. After being deployment and bending along its longitudinal axis, the monolithic device 700 is retrievable. The spacing between the curved interconnecting members 750 and 752 is maintained between about least 0.1 and 20 microns, and the spacing between the peaks 744 and the troughs 746 of the first and second Z patterns 740, 742 is maintained between about at least 0.1 and 20 microns to permit blood flow therebetween. The monolithic device 700 is able to bend, while the wall thickness of the monolithic device 700 is between about 0.1-100.0 microns.

Figure 10:
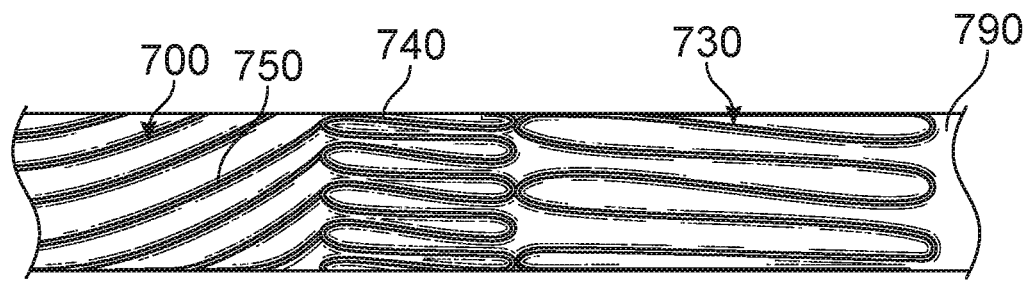
FIG. 10 is an enlarged side view of a photograph of one embodiment of the monolithic device crimped around a guidewire.

As shown in FIG. 10, the monolithic device 700 may be crimped around a guide wire 790. The crimping may collapse the first Z pattern 740, the end ring 730, and the curved interconnecting members 750 to a diameter between about 0.2 and 2.0 mm. After the monolithic device 700 is uncrimped, the monolithic device 700 may expand to a diameter between about 2.0 and 7.0 mm while maintaining adequate radial force and wall apposition. In one embodiment, the wall thickness of the monolithic device 700 is less than about 75 microns.

Figure 11A:
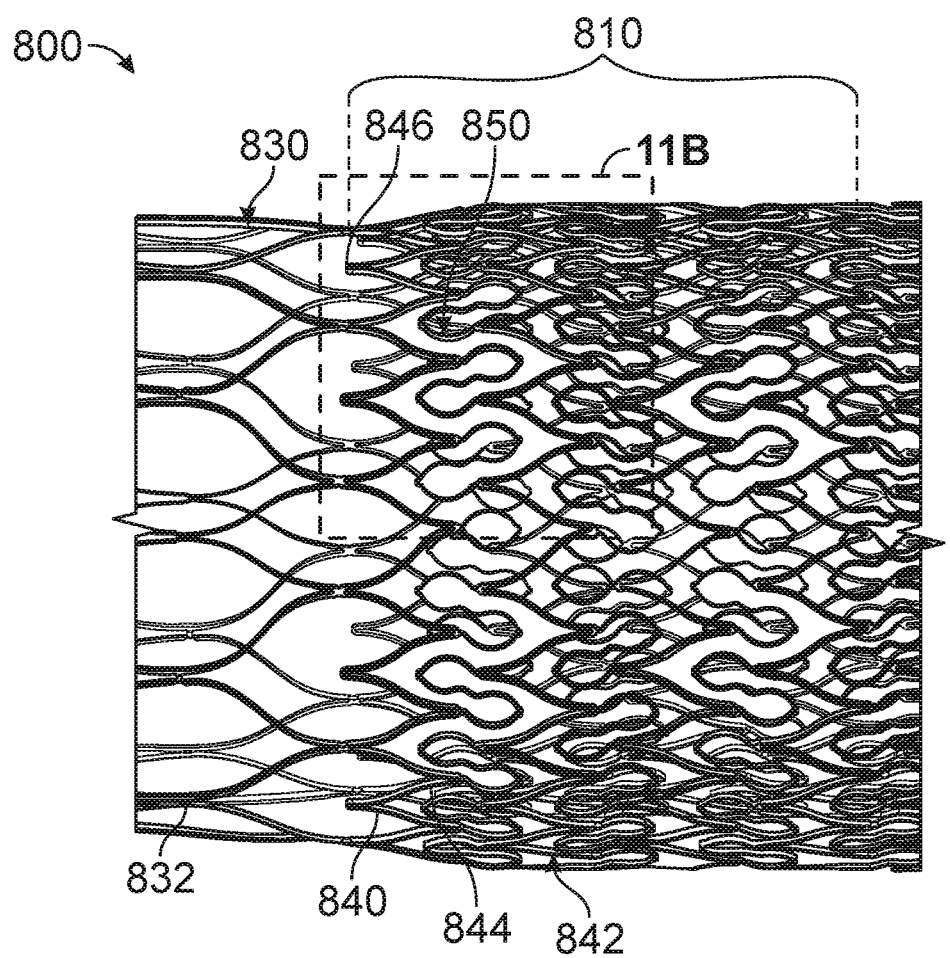
FIG. 11A is a side view of an enlarged photograph of the distal end of an alternative embodiment of the monolithic device.
Figure 11B:
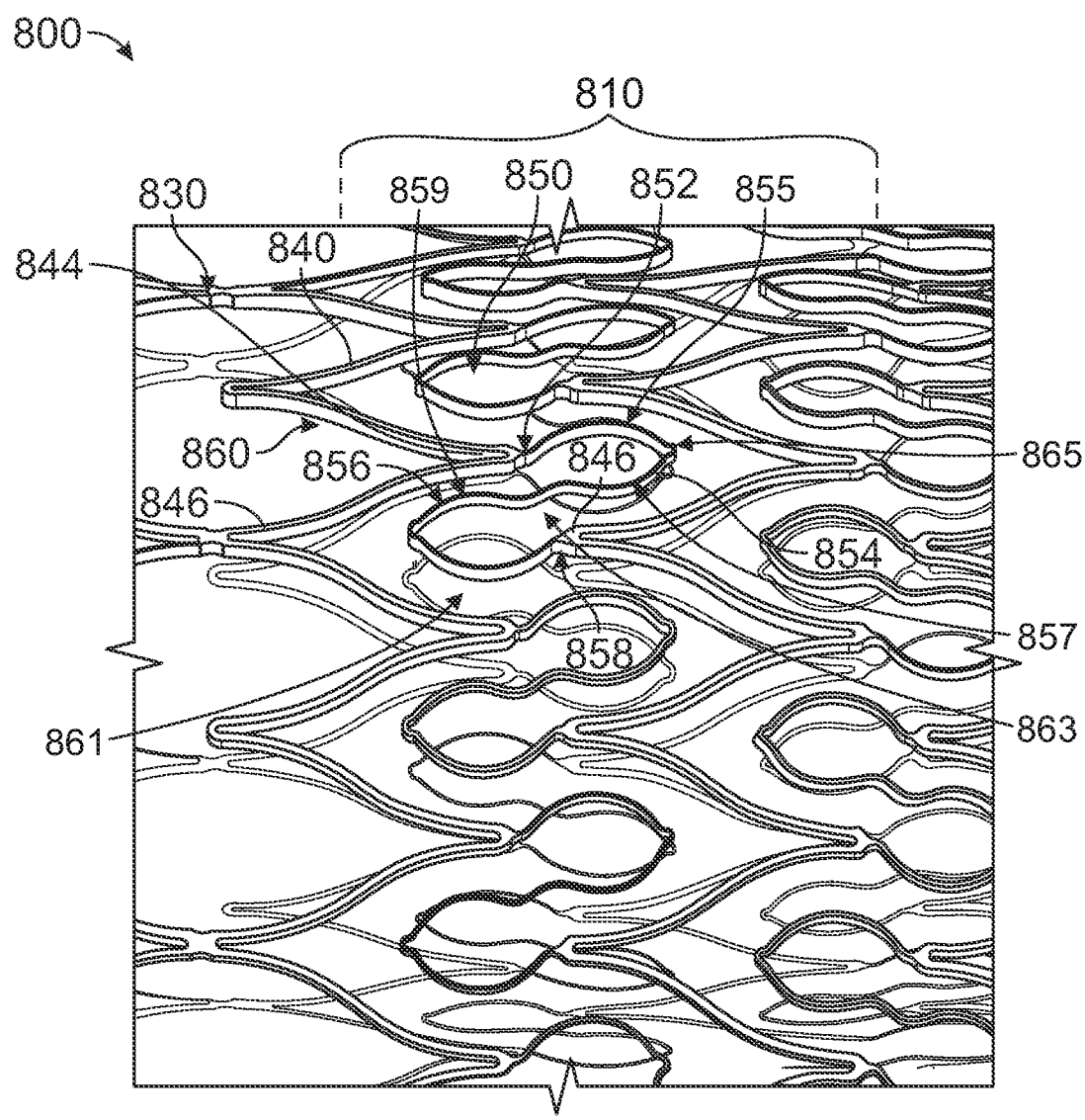
FIG. 11B is an exploded version of portion 11B from FIG. 11A of the side view of the distal end of an alternative embodiment of the monolithic device.
Figure 11C:
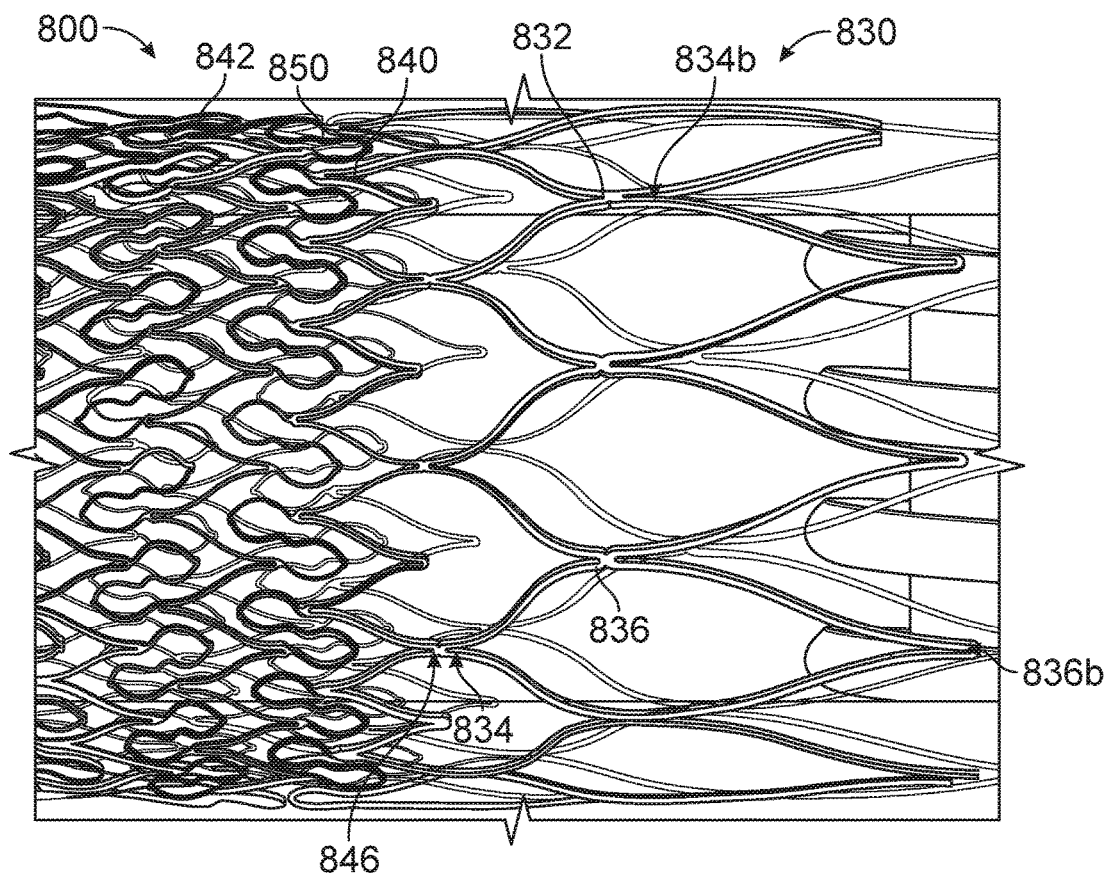
FIG. 11C is a side view of an enlarged photograph of the distal end of the alternative embodiment of the monolithic device of FIG. 11A.

An alternative embodiment of the monolithic device is shown in FIGS. 11A-11C. The monolithic device 800 comprises a dense cell pattern 810 and may include circumferential ring members comprising a first Z pattern 840, a second Z pattern 842, and a plurality of looped or generally S-shaped interconnecting members 850 connecting the first Z pattern 840 and the second Z pattern 842. The proximal and/or distal end of the monolithic device 800 may include an end ring 830 in an end Z pattern 832 that is connected to the first Z pattern 840. The first and second Z patterns 840, 842 include a plurality of interconnected peaks 844 and troughs 846. As shown in FIG. 11B, the peak 844 of the first Z pattern 840 is connected to the first end 852 of the looped or S-shaped interconnecting member 850, whereby the first end 852 of the looped or S-shaped interconnected member 850 forms a generally first loop or first generally elliptical section 854 facing the proximal end of the monolithic device 800, while the first loop or first generally elliptical section 854 connects to a second loop or second generally elliptical section 856 that faces in the opposite direction of the first loop or first generally elliptical section 854 and towards the distal end of the monolithic device. The second loop or second generally elliptical section 856 ends at the second end 858 that is connected to the trough 846 of the second Z pattern 842. In one embodiment, the first loop or first generally elliptical section 854 fits within the peak 844 of the second Z pattern 844, and the second loop or second generally elliptical section 856 fits within the trough 846 of the first Z pattern 840. As shown in FIG. 11C, the end ring 830 includes an end Z pattern 832, which includes a plurality of interconnected peaks 834 and troughs 836. The peak 834 of the end Z pattern 832 connects with the trough 846 of the first Z pattern 840, and in one embodiment, the peak 834 of the end Z pattern 832 connects with every other trough 846 of the first Z pattern 840, or every third trough 846 of the first Z pattern 840. Optionally, the end Z pattern 832 may include additional peaks 834b and troughs 836b, whereby the peaks 834b are to the troughs 836, as to further extend the distal end. A radiopaque layer 860 of Tantalum may be between two layers of metal for the monolithic device 800. The Tantalum is the white layer 860 that appears as a stripe along the side walls of the stent, as shown in FIG. 11B. Alternatively, radiopaque layer 860 may comprise another biocompatible radiopaque material.

In some embodiments, the monolithic device is formed from a material that is a metal, a polymer, a composite, or a ceramic material. In some embodiments, materials to make the inventive stents are chosen for their biocompatibility, mechanical properties, i.e., tensile strength, yield strength, and their ease of deposition include the following: elemental titanium, vanadium, aluminum, nickel, tantalum, zirconium, chromium, silver, gold, silicon, magnesium, niobium, scandium, platinum, cobalt, palladium, manganese, molybdenum and alloys thereof, such as zirconium-titanium-tantalum alloys, nitinol, and stainless steel.

In some embodiments as described above and shown in further detail in FIGS. 11A-11C, the first generally elliptical section 854 has a major axis generally parallel to a longitudinal axis of the intravascular stent device. The first generally elliptical section further comprises a first portion 855 connected to a peak of a first circumferential ring member at a first end of the major axis and to a second portion 857 at a second end of the major axis. The second portion 857 is further coupled to the second generally elliptical section 856 proximate to the first end of the major axis. Additionally, the second generally elliptical section 856 has a second major axis generally parallel to a longitudinal axis of the intravascular stent device and circumferentially off-set from the major axis. The second generally elliptical section 856 further comprises a third portion 859 coupled to the first generally elliptical section 854 proximate a second end of the second major axis and further coupled to a fourth portion 861 at a first end of the second major axis. The fourth portion 861 is further connected to a peak of the second circumferential ring member at the second end of the second major axis.

In additional embodiments as described above and shown in further detail in FIGS. 11A-11C, the intravascular stent device further comprises a curvilinear member 863 connecting the second portion 857 of the first generally elliptical section 854 to the third portion 859 of the second generally elliptical section 856. The curvilinear member 863 is oriented generally along a longitudinal axis of the intravascular stent device.

In yet additional embodiments as described above and shown in further detail in FIGS. 11A-11C, the intravascular stent device further comprises hinge regions 865 at the junctions of the portions of the generally elliptical sections. For example, a hinge region 865 interconnects the first portion 855 and the second portion 857 of the first generally elliptical section 854 at the second end of the major axis of the first generally elliptical section 854 and a second hinge region 865 interconnects the third portion 859 and the fourth portion 861 of the second generally elliptical section 856 at the first end of the major axis connect of the second generally elliptical section 856.

In some embodiments, the monolithic device 700 may be fabricated by a procedure, as described in U.S. application Ser. No. 13/788,081, filed Mar. 7, 2013 or in U.S. patent application Ser. No. 13/099,980, filed May 3, 2011, herein incorporated by reference in their entireties. In one embodiment, a coating of deposited metal film or polymer is about 0.1-100.0 microns in a tube form, which is laser cut using ultra short pulsed femtosecond laser to minimize heat affected zones and recast. The final monolithic device may be heat treated to optimize spring back effects. The stent's one piece construction allows many advantages over many currently available braided stent designs, such as a lower profile, self-expanding, and ease of manufacturing. Alternatively, the monolithic device may be produced from drawn metal or polymer tubing, wrought tubing, provided that fatigue life is adequate. Radiopaque markers could be added as an interdispersed deposited layer if vacuum deposition is used. Different metal layers may be used to form the monolithic device.

In some embodiments, the method further comprises the step of patterning at least one surface of the monolithic device. In some embodiments, the patterning comprises laser patterning to impart at least one feature on the at least one surface of the monolithic device. In some embodiments, the pattern is a series of grooves on at least one surface of the monolithic device, preferably the surface that will comprise the inner diameter of the finished stent. In other embodiments, the pattern may be a plurality of microgrooves imparted onto the luminal and/or abluminal surface of the monolithic device, as is more fully described in U.S. patent application Ser. No. 13/654,923, filed Oct. 18, 2012, which is commonly assigned with the present application and is hereby incorporated by reference in its entirety. The plurality of microgrooves may be formed either as a post-deposition process step, such as by etching, or during deposition, such as by depositing the stent-forming material onto a mandrel which has a microtopography on the surface thereof which causes the metal to deposit with the microgroove pattern as part of the deposited material.

The inventive monolithic devices may be intravascular stents, stent-grafts, grafts, heart valves, venous valves, filters, occlusion devices, catheters, sheaths, osteal implants, implantable contraceptives, implantable antitumor pellets or rods, shunts and patches, pacemakers, needles, temporary fixation rods, medical wires or medical tubes for any type of medical device, or other implantable medical devices, as will also be hereinafter described. A pacemaker (or artificial pacemaker, so as not to be confused with the heart's natural pacemaker) is a medical device that uses electrical impulses, delivered by electrodes contacting the heart muscles, to regulate the beating of the heart. The electrodes may be covered by tubing or other material that includes a surface that may require endothelialization and grooves thereon. Earrings and other piercings may benefit from the topographical features, as well as any other implant, whether the implant is an organic, inorganic, mechanical, electrical, or biological device.

The monolithic device may be used with any type of cell, which cell has a cellular membrane. Most distinct cell types arise from a single totipotent cell that differentiates into hundreds of different cell types during the course of development. Multicellular organisms are composed of cells that fall into two fundamental types: germ cells and somatic cells. During development, somatic cells will become more specialized and form the three primary germ layers: ectoderm, mesoderm, and endoderm. After formation of the three germ layers, cells will continue to specialize until they reach a terminally differentiated state that is much more resistant to changes in cell type than its progenitors. The ectoderm differentiates to form the nervous system (spine, peripheral nerves and brain), tooth enamel and the epidermis (the outer part of integument). It also forms the lining of mouth, anus, nostrils, sweat glands, hair and nails. The endoderm forms the gastrointestinal tract cells, the respiratory tract cells, the endocrine glands and organ cells, the auditory system cells, and the urinary system cells. The mesoderm forms mesenchyme (connective tissue), mesothelium, non-epithelial blood cells and coelomocytes. Mesothelium lines coeloms; forms the muscles, septa (cross-wise partitions) and mesenteries (length-wise partitions); and forms part of the gonads (the rest being the gametes).

In one embodiment, the apparatus comprises: an ultra-dense stent cell pattern including a plurality of structural members that diverts the majority of blood flow without restricting blood flow completely.

While the invention has been described in connection with various embodiments, it will be understood that the invention is capable of further modifications. This application is intended to cover any variations, uses or adaptations of the invention following, in general, the principles of the invention, and including such departures from the present disclosure as, within the known and customary practice within the art to which the invention pertains.

What is claimed is:
1. An intravascular stent device comprising:
a plurality of circumferential ring members, each circumferential ring member having a plurality of struts defining a Z-pattern having a plurality of peaks defined by vertices formed from interconnecting adjacent struts and a plurality of troughs defined by an open space bounded by three sequential vertices, the plurality circumferential ring members are positioned along a longitudinal axis of the intravascular stent device in a spaced apart relationship relative to each other;

a plurality of generally S-shaped second members, each of the plurality of generally S-shaped second members having a first elliptical section and a second elliptical section, the first elliptical section being connected to a peak of a first circumferential ring member and the second elliptical section being connected to a circumferentially adjacent peak of a second circumferential ring member longitudinally adjacent the first circumferential ring member; and wherein, when the intravascular stent device is in an expanded state, the first elliptical section is positioned between circumferentially adjacent peaks of the second circumferential ring member and nested within the open space of a trough of the second circumferential ring member and the second elliptical section is positioned between circumferentially adjacent peaks of the first circumferential ring member and nested within a trough of the open space of the first circumferential ring member.

2. The device of claim 1, further comprising an end ring member including an end Z-pattern comprising a plurality of peaks and a plurality of troughs.

3. The device of claim 2, wherein each peak of the end Z-pattern is connected to every third trough of an adjacent Z-pattern member.

4. The device of claim 1, wherein in a deployed state of the device, circumferential spacing between adjacent second members is between about 0.1 and 20 microns.

5. The device of claim 1, wherein the intravascular stent device has a wall thickness between about 0.1 and 100 microns, and wherein the intravascular stent device is configured to have a crimped state wherein the device has a diameter between about 0.2 and 2.0mm, and an expanded state wherein the intravascular stent device has a diameter between about 2.0 and 7.0 mm.

6. The device of claim 1, wherein the first elliptical section of a second member comprises an incomplete elliptical shape having an opening that faces an end of the intravascular stent device, and the second elliptical section comprises an incomplete elliptical shape having an opening that faces an opposing end of the intravascular stent device.

7. The device of claim 1, further comprising a first terminal Z-pattern member positioned at a proximal end of the intravascular stent and second terminal Z-pattern member positioned at a distal end of the intravascular stent device, wherein the first and second terminal Z-pattern members are joined to peaks of the proximal and distal ends, respectively.

8. The device of claim 7, wherein each of the first and second terminal end members further comprise a plurality of Z-pattern ring members having a length in the longitudinal axis of the intravascular stent device greater than a length of the first and second terminal Z-pattern members.

9. The device of claim 1, wherein the intravascular stent device is configured to be capable of delivery to a neurovascular site and is a flow diverter intravascular stent.

10. The intravascular stent device of claim 1 wherein:

the first elliptical section has a major axis generally parallel to a longitudinal axis of the intravascular stent device, the first elliptical section further comprises a first portion connected to a peak of a first circumferential ring member at a first end of the major axis and to a second portion at a second end of the major axis, the second portion is coupled to the second elliptical section proximate to the first end of the major axis; and the second elliptical section has a second major axis generally parallel to a longitudinal axis of the intravascular stent device and circumferentially off-set from the major axis, the second generally elliptical section further comprises a third portion coupled to the first generally elliptical section proximate a second end of the second major axis and further coupled to a fourth portion at a first end of the second major axis, the fourth portion connected to a peak of the second circumferential ring member at the second end of the second major axis.

11. The device of claim 10, further comprising a curvilinear member connecting the second portion of the first elliptical section to the third portion of the second elliptical section, the curvilinear member being oriented generally along a longitudinal axis of the intravascular stent device.

* * * * *